(12) United States Patent
Chelvayohan

(10) Patent No.: US 6,998,628 B2
(45) Date of Patent: Feb. 14, 2006

(54) METHOD OF MEDIA TYPE DIFFERENTIATION IN AN IMAGING APPARATUS

(75) Inventor: Mahesan Chelvayohan, Lexington, KY (US)

(73) Assignee: Lexmark International, Inc., Lexington, KY (US)

( * ) Notice: Subject to any disclaimer, the term of this patent is extended or adjusted under 35 U.S.C. 154(b) by 221 days.

(21) Appl. No.: 10/301,176

(22) Filed: Nov. 21, 2002

(65) Prior Publication Data

US 2004/0099822 A1 May 27, 2004

(51) Int. Cl.
G01N 21/86 (2006.01)

(52) U.S. Cl. ............................. 250/559.01; 250/559.39; 356/612; 356/448; 347/106; 347/16; 347/19

(58) Field of Classification Search .......... 250/559.39, 250/55, 9.4; 356/601, 612, 445, 448; 347/16, 347/19, 106; 399/45
See application file for complete search history.

(56) References Cited

U.S. PATENT DOCUMENTS

| | | | | |
|---|---|---|---|---|
| 3,932,755 A | * | 1/1976 | Sagawa | 250/349 |
| 4,540,887 A | | 9/1985 | Minerd et al. | 250/561 |
| 4,721,968 A | | 1/1988 | Arai et al. | 346/136 |
| 4,723,072 A | * | 2/1988 | Naruse | 235/454 |
| 4,774,551 A | | 9/1988 | Amos et al. | 355/68 |
| 4,983,854 A | * | 1/1991 | Mizuno et al. | 250/559.15 |
| 5,084,627 A | * | 1/1992 | Ueki et al. | 250/559.4 |
| 5,122,833 A | | 6/1992 | Sato | 355/203 |
| 5,139,339 A | | 8/1992 | Courtney et al. | 356/446 |
| 5,329,338 A | | 7/1994 | Merz et al. | 355/207 |
| 5,354,995 A | | 10/1994 | Endo et al. | 250/561 |
| 5,508,521 A | | 4/1996 | Kraft et al. | 250/574 |
| 5,751,443 A | | 5/1998 | Borton et al. | 356/446 |
| 5,764,251 A | * | 6/1998 | Hashimoto | 347/16 |
| 5,806,992 A | | 9/1998 | Ju | 400/56 |
| 6,018,164 A | | 1/2000 | Mullens | 250/559.4 |
| 6,079,807 A | | 6/2000 | Lindstrom et al. | 347/16 |
| 6,121,989 A | | 9/2000 | Song | 347/218 |
| 6,144,811 A | | 11/2000 | Ohori et al. | 399/9 |
| 6,217,168 B1 | | 4/2001 | Elgee | 347/105 |
| 6,291,829 B1 | | 9/2001 | Allen et al. | 250/559.07 |
| 6,323,966 B1 | | 11/2001 | DeCaro et al. | 358/475 |
| 6,386,676 B1 | | 5/2002 | Yang et al. | 347/19 |
| 2004/0075067 A1 | * | 4/2004 | McAuliffe | 250/559.4 |

* cited by examiner

Primary Examiner—David Porta
Assistant Examiner—Stephen Yam
(74) Attorney, Agent, or Firm—Taylor & Aust, P.C.

(57) ABSTRACT

A method of media type differentiation includes the steps of providing a media sensor including a specular detector that provides a specular signal output having a signal level related to an amount of the reflected specular light received; providing a highly reflective surface positioned to face the media sensor; interposing a print media sheet between the media sensor and the highly reflective surface; using the media sensor to measure a first amount of the reflected specular light and determining a first signal level of the specular signal output of the specular detector; and using the first signal level to differentiate the print media sheet as being one of a transparency media sheet or a high glossy media sheet.

16 Claims, 4 Drawing Sheets

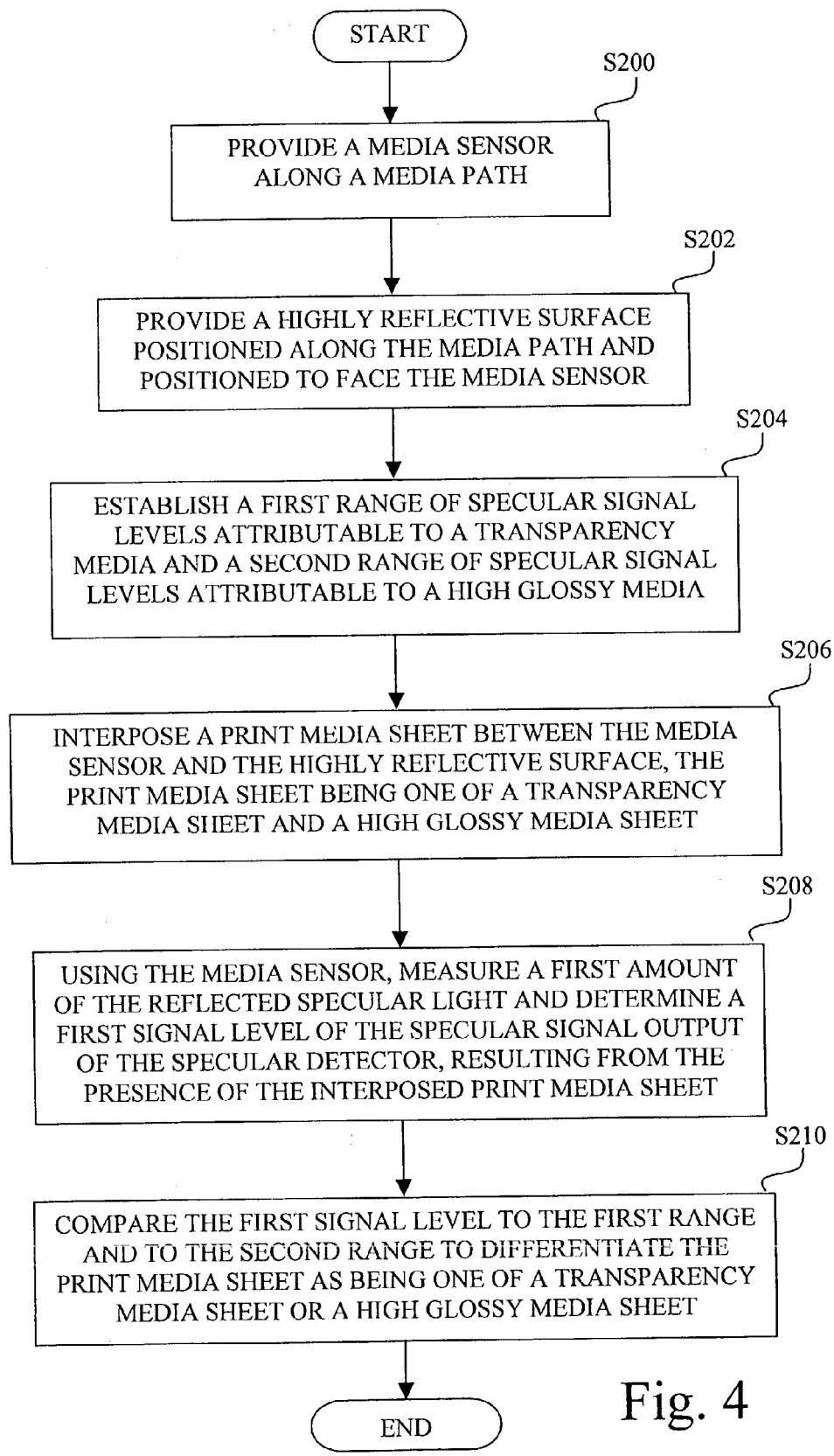

ns sheet, the normalized reflectance ratio Rn
METHOD OF MEDIA TYPE DIFFERENTIATION IN AN IMAGING APPARATUS

BACKGROUND OF THE INVENTION

1. Field of the Invention

The present invention relates to print media detection, and, more particularly, to a method of media type differentiation, such as distinguishing between high glossy media and transparency media, in an imaging apparatus.

2. Description of the Related Art

Various attempts have been made to try to sense when paper is being processed through a printer. One such attempt distinguishes between the presence and absence of paper by providing a high contrast ratio sensor including a light emitter and a pair of photodetectors functioning as a diffuse detector and a reflective detector. The two photodetectors are connected in a manner to cause the diffuse detector output to subtract from the reflective (or transmissive) detector output. This subtraction of signals provides a high contrast ratio. The pair of photodetectors may be located on the same side of the print medium as the light emitter, and a mirror may be positioned on the opposite side of the paper to aid in detecting the presence of the sheet of paper.

More recently, media sensors have been used to detect the type of media in an imaging device, such as an ink jet printer, by optically measuring the glossiness of the media using a media sensor detecting each of specularly reflected light and diffusely scattered light. To measure the glossiness, a collimated beam of light is directed towards the media and a reflectance ratio (R) of the detected reflected specular light intensity and the detected diffusively scattered light intensity is calculated. The media sensor is initially calibrated by measuring a reflectance ratio (R0) on a known gloss media. A normalized reflectance ratio (Rn) is calculated using the formula: Rn=(R/R0). Normalized reflectance ratio Rn then is used to identify the media type of an unknown media by a comparison of the normalized reflectance ratio Rn to a plurality of normalized reflectance ratio Rn ranges, each range being associated with a particular type of media. For example, if the media sensor is calibrated with a perfectly diffuse media, then the normalized reflectance ratio Rn ranges might be established as in the following table.

TABLE 1

Media Determination Based on Normalized Reflectance Ratio Rn

| Rn Range | Media Type |
| --- | --- |
| Rn < 1.5 | Coated Paper |
| 1.5 ≦ Rn < 3 | Plain Paper |
| 3 ≦ Rn < 10 | Photo Paper |
| 10 ≦ Rn | Transparency |

In practice, however, it may be quite difficult using the normalized reflectance ratio range approach to distinguish between a high glossy media sheet, such as a high gloss photo paper, and a transparency media sheet. Further, the normalized reflectance ratio approach requires both a specular detector and a diffuse detector.

What is needed in the art is an improved media sensing apparatus that can reliably distinguish between high glossy media and transparency media.

SUMMARY OF THE INVENTION

The present invention relates to an improved media sensing apparatus that can reliably distinguish between high glossy media and transparency media.

The present invention, in one form thereof, is directed to a method of media type differentiation. A media sensor is provided including a specular detector that provides a specular signal output having a signal level related to an amount of the reflected specular light received. A highly reflective surface is positioned to face the media sensor. A print media sheet is interposed between the media sensor and the highly reflective surface. The print media sheet is one of a transparency media sheet and a high glossy media sheet. The media sensor is used to measure a first amount of the reflected specular light and to determine a first signal level of the specular signal output of the specular detector. The first signal level is used to differentiate the print media sheet as being one of the transparency media sheet or the high glossy media sheet.

In another form thereof, the present invention is directed to an imaging apparatus. The imaging apparatus includes a mid-frame defining, in part, a media path. A media sensor is positioned along the media path. The media sensor includes a light source for generating a light beam, and a specular detector positioned in relation to the light source for receiving reflected specular light, the specular detector providing a specular signal output having a signal level related to an amount of the reflected specular light received by the specular detector. A highly reflective surface is positioned along the media path, the highly reflective surface being positioned to face the media sensor. A feed roller unit is provided for transporting a sheet of print media along the media path. A controller is provided communicatively coupled to the media sensor and to the feed roller unit. The controller executes program instruction for performing the steps of accessing a first range of specular signal levels attributable to a transparency media and a second range of specular signal levels attributable to a high glossy media; interposing a print media sheet between the media sensor and the highly reflective surface; using the media sensor to measure a first amount of the reflected specular light and determining a first signal level of the specular signal output of the specular detector, resulting from the presence of the interposed print media sheet; and comparing the first signal level to the first range and to the second range to differentiate the print media sheet as being one of a transparency media sheet or a high glossy media sheet.

In another form thereof, the present invention is directed to a method of media type differentiation in an imaging apparatus. The method includes the steps of providing a media sensor along a media path, the media sensor including a light source for generating a light beam, and a detector positioned in relation to the light source for receiving reflected light, the detector providing a signal output having a signal level related to an amount of the reflected light received by the detector; providing a highly reflective surface positioned along the media path of the imaging apparatus, the highly reflective surface being positioned to face the media sensor; establishing a first range of signal levels attributable to a transparency media and a second range of signal levels attributable to a high glossy media; interposing a print media sheet between the media sensor and the highly reflective surface, the print media sheet being one of a transparency media sheet and a high glossy media sheet; following the interposing step, using the media sensor to measure a first amount of the reflected light and determining a first signal level of the signal output of the detector, resulting from the interposed print media sheet; and comparing the first signal level to the first range and to the second range to differentiate the print media sheet as being one of the transparency media sheet or the high glossy media sheet.

An advantage of the present invention is that it can be implemented relatively easily in any imaging device using a simple sensor and a reflective surface, such as a reflective tape applied to a portion of a mid-frame.

Another advantage of the present invention is that the same sensor used for printhead alignment and/or general media detection can be adapted to distinguish between high glossy media and transparency media.

Another advantage is that the present invention can be implemented with little additional hardware costs in an imaging device having a preexisting sensor positioned adjacent to a print media path.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 4 is a flowchart of a method of the invention.

Corresponding reference characters indicate corresponding parts throughout the several views. The exemplifications set out herein illustrate one preferred embodiment of the invention, and such exemplifications are not to be construed as limiting the scope of the invention in any manner.

DETAILED DESCRIPTION OF THE INVENTION

Figure 1:
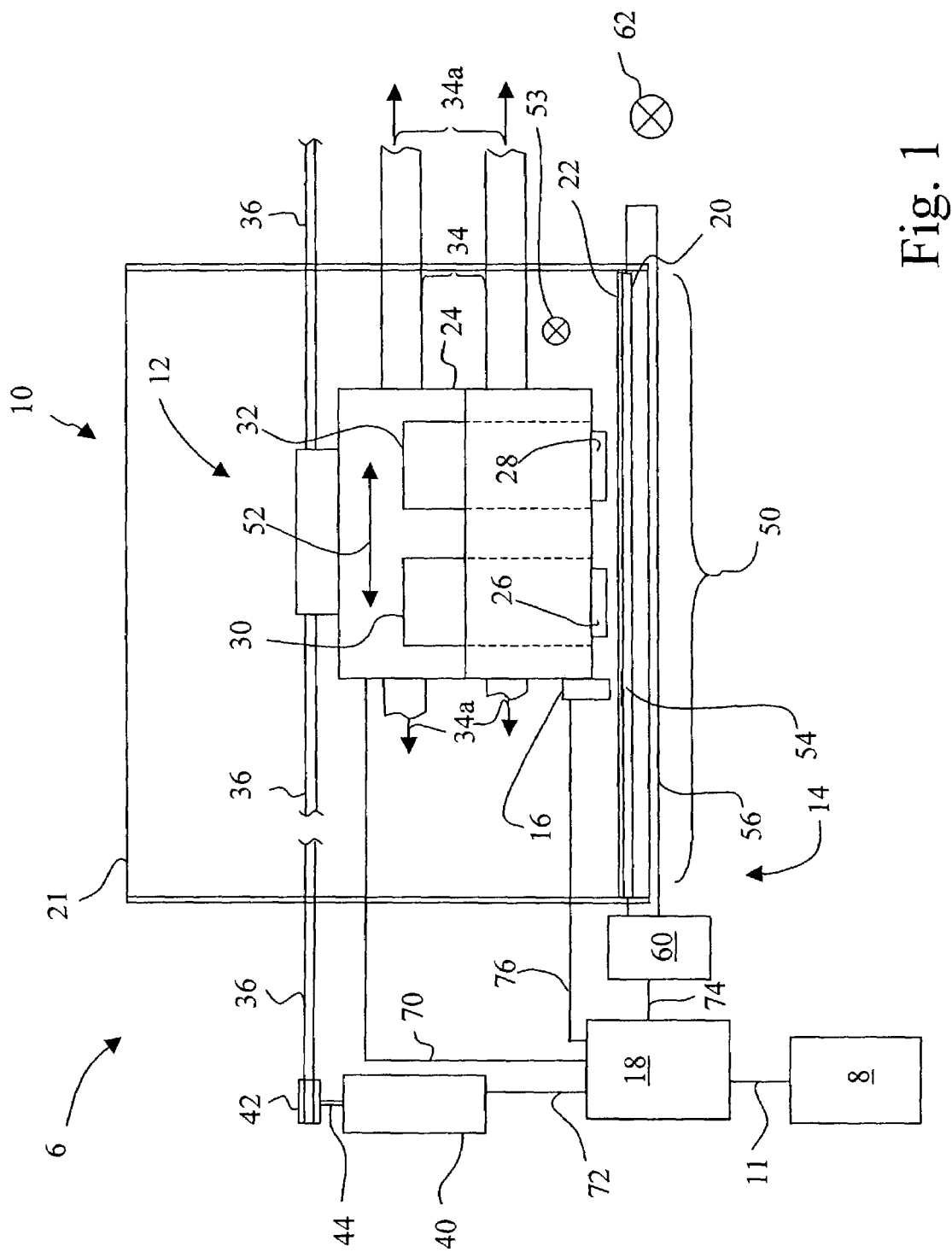
FIG. 1 is a diagrammatic representation of an imaging system embodying the present invention.
Figure 2:
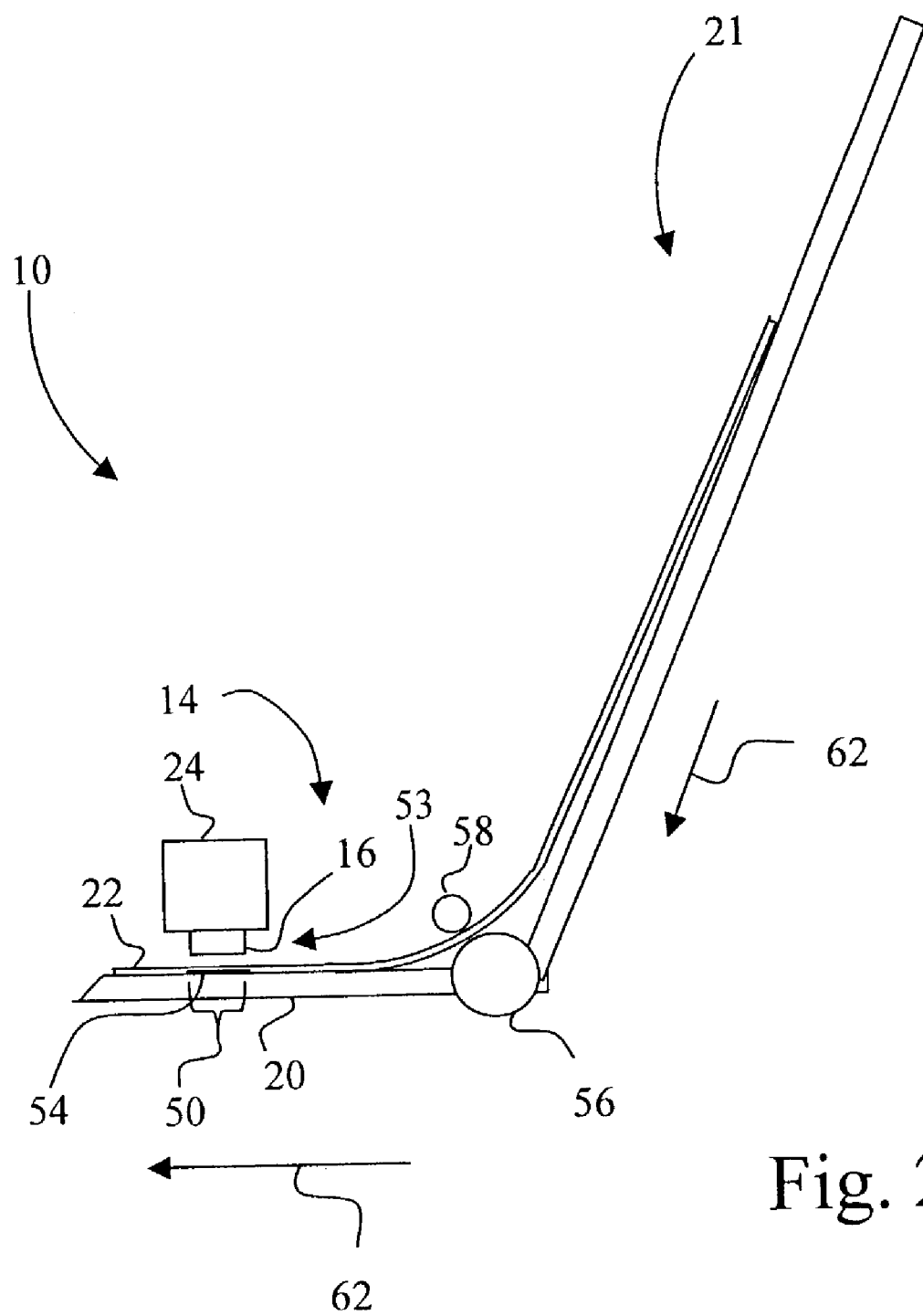
FIG. 2 is a side diagrammatic representation of a portion of the ink jet printer of the imaging system of FIG. 1.

Referring now to the drawings, and particularly to FIGS. 1 and 2, there is shown an imaging system 6 embodying the present invention. Imaging system 6 includes a computer 8 and an imaging apparatus in the form of an ink jet printer 10. Computer 8 is communicatively coupled to ink jet printer 10 via a communications link 11. Communications link 11 may be, for example, a direct electrical or optical connection, or a network connection.

Computer 8 is typical of that known in the art, and includes a display, an input device, e.g., a keyboard, a processor, and associated memory. Resident in the memory of computer 8 is printer driver software. The printer driver software places print data and print commands in a format that can be recognized by ink jet printer 10.

Ink jet printer 10 includes a printhead carrier system 12, a feed roller unit 14, a media sensor 16, a controller 18, a mid-frame 20 and a media source 21.

Media source 21 is configured to receive a plurality of print media sheets from which an individual print media sheet 22 is supplied to feed roller unit 14, which in turn further transports print media sheet 22 during a printing operation. Print media sheet 22 can be, for example, coated paper, plain paper, high glossy media and transparency media. High glossy media may be, for example, a high gloss photo paper.

Printhead carrier system 12 includes a printhead carrier 24 for carrying a color printhead 26 and a black printhead 28. A color ink reservoir 30 is provided in fluid communication with color printhead 26, and a black ink reservoir 32 is provided in fluid communication with black printhead 28. Printhead carrier system 12 and printheads 26, 28 may be configured for unidirectional printing or bi-directional printing.

Mounted to printhead carrier 24 is media sensor 16. In the context of the present invention, media sensor 16 is used to differentiate between various types of media, and in particular, to differentiate between transparency media and high glossy media. Media sensor 16 may, however, also be used to perform other sensing functions, such as for example, during printhead alignment.

Printhead carrier 24 is guided by a pair of guide rods 34. The axes 34a of guide rods 34 define a bi-directional scanning path for printhead carrier 24, and thus, for convenience the bi-directional scanning path will be referred to as bi-directional scanning path 34a. Printhead carrier 24 is connected to a carrier transport belt 36 that is driven by a carrier motor 40 via carrier pulley 42. Carrier motor 40 has a rotating carrier motor shaft 44 that is attached to carrier pulley 42. At the directive of controller 18, printhead carrier 24 is transported in a reciprocating manner along guide rods 34. Carrier motor 40 can be, for example, a direct current (DC) motor or a stepper motor.

The reciprocation of printhead carrier 24 transports ink jet printheads 26, 28 and media sensor 16 across the sheet of print media 22, such as paper, along bi-directional scanning path 34a to define a print zone 50 of printer 10. Due to the presence of media sensor 16 on printhead carrier 24, print zone 50 also defines a media detection zone, which for convenience will be referred to using the same element number 50 as used for the print zone. The reciprocation of printhead carrier 24 occurs in a main scan direction 52 that is parallel with bi-directional scanning path 34a, and is also commonly referred to as the horizontal direction. During each scan of printhead carrier 24, the sheet of print media 22 is held stationary by feed roller unit 14.

Mid-frame 20 provides support for the sheet of print media 22 when the sheet of print media 22 is in print zone 50, and in part, defines a portion of a print media path 53 of ink jet printer 10. Mid-frame 20 includes a highly reflective surface 54, such as for example, a reflective sticker (a tape having an adhesive surface and a reflective surface), an aluminum foil strip, or a mirror, that is located along print media path 53 and in print zone 50 along bi-directional scanning path 34a. Highly reflective surface 54 defines within media detection zone 50 a transparency detection zone where discrimination between high glossy media and transparency media will occur. The term "highly reflective surface" is used to mean a surface having a reflectivity, for example, of about 70 percent or greater.

Referring to FIG. 2, feed roller unit 14 includes an index roller 56 and corresponding index pinch rollers 58. Index roller 56 is driven by a drive unit 60 (FIG. 1). Index pinch rollers 58 apply a biasing force to hold the sheet of print media 22 in contact with respective driven index roller 56. Drive unit 60 includes a drive source, such as a stepper motor, and an associated drive mechanism, such as a gear train or belt/pulley arrangement. Feed roller unit 14 feeds the sheet of print media 22 in a sheet feed direction 62 (see FIGS. 1 and 2).

Controller 18 is electrically connected and communicatively coupled to printheads 26 and 28 via a printhead interface cable 70. Controller 18 is electrically connected and communicatively coupled to carrier motor 40 via an interface cable 72. Controller 18 is electrically connected and communicatively coupled to drive unit 60 via an interface cable 74. Controller 18 is electrically connected and communicatively coupled to media sensor 16 via a communications link 76.

Controller 18 includes a microprocessor having an associated random access memory (RAM) and read only memory (ROM). Controller 18 executes program instructions to effect the printing of an image on the sheet of print media 22, such as coated paper, plain paper, high glossy media and transparency media. In addition, controller 18 executes instructions to conduct media sensing, and in particular with respect to the present invention, to conduct differentiation between high glossy media and transparency media.

Figure 3:
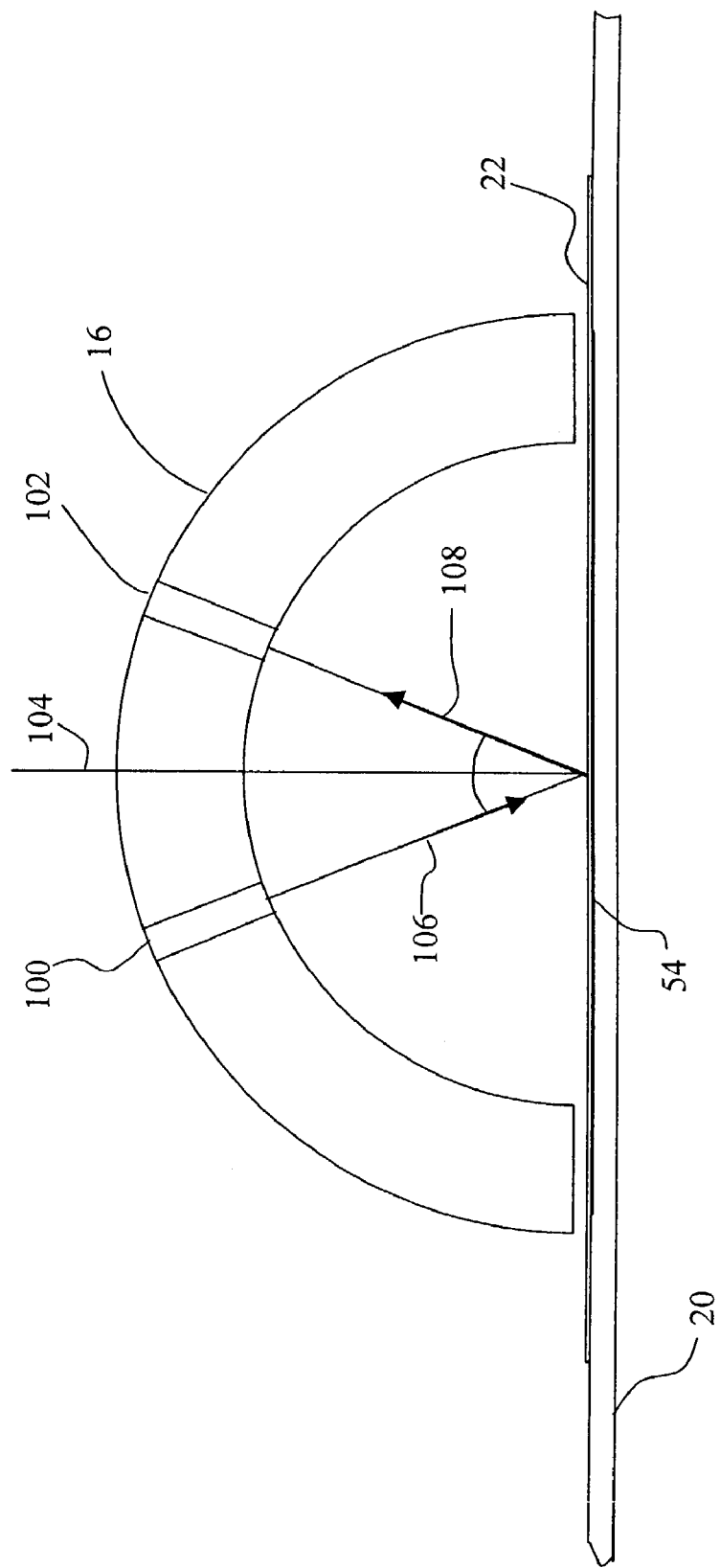
FIG. 3 is a diagrammatic representation of a media sensor arrangement used with the present invention.

Referring to FIG. 3, media sensor 16 may be, for example, a unitary optical sensor including a light source 100 and a specular detector 102, each positioned to establish an angle of incidence or a specular angle of reflection, respectively, of about 25 degrees with respect to normal line 104. In its simplest form, light source 100 may include, for example, a light emitting diode (LED). In a more complex form, light source 100 may further include additional optical components for generating a collimated light beam, such as light beam 106. Specular detector 102 can be, for example, a phototransistor whose voltage, or current, output varies as a function of the intensity of the reflected specular light 108 that it receives.

As shown in FIG. 3, light source 100 and specular detector 102 are located to be on the same side of the sheet of print media 22. However, highly reflective surface 54 is positioned to be on the opposite side of print media 22.

For general media detection, it is possible to position media sensor 16 in print zone 16 at any position which will allow print media sheet 22 to receive and reflect light. If, however, it is desired to be able to distinguish between transparency media and high glossy media, then printhead carrier 24 is moved to position media sensor 16 in opposition to highly reflective surface 54, such that reflective surface 54 faces media sensor 16. For this determination to occur, print media sheet 22 is advanced into media detection zone 50 until a portion of print media sheet 22 is interposed between media sensor 16 and highly reflective surface 54. Specular detector 102 generates a voltage output, or alternatively a current output, deemed a specular signal, that is digitized through an analog-to-digital converter (not shown) of controller 18 for processing by the processor of controller 18.

When light beam 106 is incident on print media sheet 22, depending on the media type, various amounts of light will be absorbed, specularly reflected, diffusely reflected or transmitted through the media. For media type detection, the specularly reflected portion is primarily used. For high glossy media and single transparency media, the amount of reflected specular light is almost equal. However, transparency media differs from high glossy media in that a sheet of transparency media transmits most of the received light through the sheet. Adding more sheets of transparency media or placing a highly reflective surface on a side of the transparency media sheet opposite to the side on which light beam 106 is incident increases the specular reflection of reflected specular light 108.

Table 2 below shows the relative magnitude of specular signals measured by a reflective sensor, such as media sensor 16, having a 25 degree angle of incidence on transparency media and high glossy media, such as photo paper. Table 2 further shows the signal level when a highly reflective surface, such as a mirror or a strip of aluminum foil, is placed behind a single transparency media sheet.

TABLE 2

Specular Signals Measured by Specular Detector

| Media Type | Specular Signal (mV) |
| --- | --- |
| Low Gloss Photo Paper | 440 |
| High Gloss Photo Paper | 860 |
| Single Transparency Sheets Without Using Highly Reflective Surface Behind Sheet | 900 |
| Two Transparency Sheet Without Using Highly Reflective Surface Behind Sheets | 1400 |
| Three Transparency Sheets Without Using Highly Reflective Surface Behind Sheets | 1900 |
| Four Transparency Sheets Without Using Highly Reflective Surface Behind Sheets | 2250 |
| Five Transparency Sheets Without Using Highly Reflective Surface Behind Sheets | 2500 |
| Single Transparency Sheet With Using Highly Reflective Surface, e.g., Aluminum Foil, Behind Sheet | 4500 |

As shown in Table 2, the specular signal for the range of low gloss photo paper to high gloss photo paper will typically vary from about 440 millivolts (mV) to about 860 mV on this scale. The detection of a single transparency media sheet yields a specular signal about 900 mV, which is only slightly above that of high gloss photo paper (i.e., high glossy media) when no highly reflective surface, such as highly reflective surface 54, is used. However, as shown in Table 2, placement of highly reflective surface 54, such as an aluminum foil, behind the transparency media sheet increases the signal level of the specular signal to about 4500 mV.

Advantageously, adding a highly reflective surface can be very inexpensive. As illustrated in FIGS. 1 and 2, in a design where media detection is performed in the print zone, such as print zone 50, the highly reflective surface could be a reflective sticker or tape having a highly reflective surface, that is adhered by an adhesive backing to some location on mid-frame 20 in print zone 50.

A summary of the method of the present invention will now be described with respect to the flowchart of FIG. 4.

At step S200, media sensor 16 is provided along the media path 53 of the imaging apparatus, i.e., printer 10. As described above, media sensor 16 includes light source 100 for generating a light beam 106, and includes a specular detector 102 positioned in relation to light source 100 for receiving reflected specular light 108. Specular detector 102 provides a specular signal output having a signal level related to an amount of reflected specular light 108 received by specular detector 102.

At step S202, highly reflective surface 54 is positioned along the media path 53 of the imaging apparatus, i.e., printer 10. The highly reflective surface 54 is positioned to face media sensor 16.

At step S204, a first range of specular signal levels attributable to a transparency media and a second range of specular signal levels attributable to a high glossy media is established, for example based on empirical data, such as that of Table 2 above, or by calibrating the sensor to a known media. The actual values in the first and second ranges will depend on a variety of factors, such as for example, the type of components used for sensor 16, the degree of reflectivity of highly reflective surface 54, and the angle of incidence. These ranges, as well as other ranges for other media types, may be stored, for example, in the memory of controller 18 and are accessible to controller 18. As an example, in a design, such as described above with respect to FIGS. 1 and 2, where only a single sheet is being measured at a time, the range established for high glossy media may be, for example, between 800 mV and 1000 mV, and the range for a single transparency media sheet may be, for example, 300 mV and higher. Thus, the present invention can establish a dead band between the first range of specular signal levels attributable to transparency media and the second range of specular signal levels attributable to high glossy media. Controller 18 will then consider any specular signal level falling within the dead band to be invalid.

At step S206, print media sheet 22 is interposed between media sensor 16 and highly reflective surface 54. For this example, it is assumed that print media sheet 22 is one of a transparency media sheet and a high glossy media sheet.

At step S208, following the interposing step S206, media sensor 16 is used to measure the amount of reflected specular light and to determine a signal level, deemed for convenience a first signal level, of the specular signal output of specular detector 102, resulting from the presence of the interposed print media sheet 22. Controller 18 receives via communications link 76 the specular signal output, and in turn conditions and processes the specular signal output.

At step S210, controller 18 compares the first signal level determined at step S208 to the first range and to the second range to differentiate print media sheet 22 as being one of the transparency media sheet or the high glossy media sheet. For example, if the signal level is 850 mV, then it will be determined that be media type is that of a high glossy media sheet, and if the signal level is 4500 mV then it will be determined that the media type is that of a transparency media sheet.

While this invention has been described with respect to preferred embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of media type differentiation, comprising the steps of:
    providing a media sensor including a specular detector that provides a specular signal output having a signal level related to an amount of a reflected specular light received;
    providing a highly reflective surface positioned to face said media sensor, said highly reflective surface being positioned with respect to said media sensor such that said specular detector detects specular light reflections from said highly reflective surface;
    interposing a print media sheet between said media sensor and said highly reflective surface, said print media sheet being one of a transparency media sheet and a high glossy media sheet, said print media sheet being positioned with respect to said media sensor such that said specular detector detects specular light reflections from said print media sheet;
    using said media sensor to measure a first amount of said reflected specular light and determining a first signal level of said specular signal output of said specular detector; and
    using said first signal level to differentiate said print media sheet as being one of said transparency media sheet or said high glossy media sheet.

2. The method of claim 1, wherein said highly reflective surface is positioned in a print zone of an imaging apparatus.

3. The method of claim 2, wherein said highly reflective surface is positioned on a mid-frame of said imaging apparatus.

4. The method of claim 1, wherein said highly reflective surface is one of a mirror, an aluminum strip and a reflective sticker.

5. The method of claim 1, further comprising the steps of:
    establishing a first range of specular signal levels attributable to transparency media and a second range of specular signal levels attributable to high glossy media; and
    comparing said first signal level to said first range and to said second range to differentiate said print media sheet as being one of said transparency media sheet or said high glossy media sheet.

6. The method of claim 5, wherein said first range and said second range is separated by a dead band, wherein any specular signal level falling in said dead band is considered invalid.

7. An imaging apparatus, comprising:
    a mid-frame defining, in part, a media path;
    a media sensor positioned along said media path, said media sensor including a light source for generating a light beam, and a specular detector positioned in relation to said light source for receiving reflected specular light, said specular detector providing a specular signal output having a signal level related to an amount of said reflected specular light received by said specular detector;
    a highly reflective surface positioned along said media path, said highly reflective surface being positioned to face said media sensor, said highly reflective surface being positioned with respect to said media sensor such that said specular detector detects specular light reflections from said highly reflective surface;
    a feed roller unit for transporting a print media sheet along said media path; and
    a controller communicatively coupled to said media sensor and to said feed roller unit, said controller executing program instruction for performing the steps of:
    accessing a first range of specular signal levels attributable to a transparency media and a second range of specular signal levels attributable to a high glossy media;
    interposing said print media sheet between said media sensor and said highly reflective surface, said print media sheet being positioned with respect to said media sensor such that said specular detector detects specular light reflections from said print media sheet
    using said media sensor to measure a first amount of said reflected specular light and determining a first signal level of said specular signal output of said specular detector, resulting from the presence of the interposed print media sheet; and comparing said first signal level to said first range and to said second range to differentiate said print media sheet as being one of a transparency media sheet or a high glossy media sheet.

8. The imaging apparatus of claim 7, further comprising a printhead carrier defining a print zone, said highly reflective surface being positioned in said print zone.

9. The imaging apparatus of claim 8, wherein said highly reflective surface is positioned on said mid-frame of said imaging apparatus.

10. The imaging apparatus of claim 7, wherein said highly reflective surface is one of a mirror, an aluminum strip and a reflective sticker.

11. The imaging apparatus of claim 7, wherein said first range and said second range is separated by a dead band, wherein any specular signal level falling in said dead band is judged by said controller to be invalid.

12. A method of media type differentiation in an imaging apparatus, comprising the steps of:

providing a media sensor along a media path, said media sensor including a light source for generating a light beam, and a specular detector positioned in relation to said light source for receiving reflected light, said specular detector providing a signal output having a signal level related to an amount of said reflected light received by said specular detector;

providing a highly reflective surface positioned along said media path of said imaging apparatus, said highly reflective surface being positioned to face said media sensor, said highly reflective surface being positioned with respect to said media sensor such that said specular detector detects specular light reflections from said highly reflective surface;

establishing a first range of signal levels attributable to a transparency media and a second range of signal levels attributable to a high glossy media;

interposing a print media sheet between said media sensor and said highly reflective surface, said print media sheet being one of a transparency media sheet and a high glossy media sheet, said print media sheet being positioned with respect to said media sensor such that said specular detector detects specular light reflections from said print media sheet;

following said interposing step, using said media sensor to measure a first amount of said reflected light and determining a first signal level of said signal output of said specular detector, resulting from the presence of the interposed print media sheet; and comparing said first signal level to said first range and to said second range to differentiate said print media sheet as being one of said transparency media sheet or said high glossy media sheet.

13. The method of claim 12, wherein said highly reflective surface is positioned in a print zone of said imaging apparatus.

14. The method of claim 13, wherein said highly reflective surface is positioned on a mid-frame of said imaging apparatus.

15. The method of claim 12, wherein said highly reflective surface is one of a mirror, an aluminum strip and a reflective sticker.

16. The method of claim 12, wherein said first range and said second range is separated by a dead band, wherein any signal level falling in said dead band is considered invalid.

* * * * *